United States Patent [19]

Kuwata et al.

[11] Patent Number: 5,045,574

[45] Date of Patent: Sep. 3, 1991

[54] FILM-FORMING AGENT

[75] Inventors: Satoshi Kuwata, Annaka; Takashi Ohkawara, Myogi; Takaaki Shimizu, Joetsu, all of Japan

[73] Assignee: Shin-Etsu Chemical Co., Ltd., Tokyo, Japan

[21] Appl. No.: 467,387

[22] Filed: Jan. 19, 1990

[30] Foreign Application Priority Data

Jan. 26, 1989 [JP] Japan .................................. 1-18457

[51] Int. Cl.$^5$ .............................................. C08K 9/06
[52] U.S. Cl. .................................. 523/212; 523/213; 524/268; 524/588
[58] Field of Search ............... 523/212, 213; 524/268, 524/588

[56] References Cited

U.S. PATENT DOCUMENTS 2,938,009  5/1960  Lucas ................................. 524/588
3,341,490  9/1967  Burdick et al. .................... 523/212
3,565,851  2/1971  Neuroth ............................ 523/212

Primary Examiner—Paul R. Michl
Assistant Examiner—Karen A. Hellender
Attorney, Agent, or Firm—Wyatt, Gerber, Burke & Badie

[57] ABSTRACT

The film-forming agent of the invention is a blend of a silica organosol, of which the silica particles have a specified specific surface area and specified densities of surface groups including silanol groups, alkoxy groups and trimethyl silyl groups, and a diorganopolysiloxane of a specified viscosity terminated at each molecular chain end with a silanolic hydroxy group. The film-forming agent is useful as a skin-care preparation for preventing chapping of hands of people having frequent occasions of contacting with water to exhibit durable water repellency.

6 Claims, No Drawings

FILM-FORMING AGENT

BACKGROUND OF THE INVENTION

The present invention relates to a film-forming agent or, more particularly, to a film-forming agent useful as an ingredient in skin-care preparations and polishing agents or in medical uses.

It is a remarkable fact that certain people having frequent daily occasions of handling water, such as medical doctors, nurses, cooks, housewives and the like, sometimes suffer from skin chapping or inflammation on their hands and fingers because the skin on their hands and fingers is apt to be defatted by water, in particular, water containing a detergent. It is a usual practice in order to protect hands and fingers from skin chapping that a skin-care preparation is applied to the hands and fingers after contacting with water. Such a skin-care treatment is of course very troublesome if each time of water handling must be followed by application of a skin care preparation. Accordingly, several attempts and proposals have been made to develop a skin care preparation capable of exhibiting sustained water repellency (see, for example, Japanese Patent Publication 48 1503 and Japanese Patent Kokai 61-161209, 61-161211 and 61-161214).

For example, the skin-care preparation disclosed in Japanese Patent Publication 48-1503 contains a diorgano polysiloxane terminated at each molecular chain end with a trimethyl silyl group and having a relatively high viscosity. The skin care preparation of this type is not quite satisfactory in the feeling of use because, when it is applied to human skin, tackiness is felt more or less in addition to the poor sustainability of water repellency far from sufficient.

Turning now to polishing agents such as, mainly, car polishing waxes, sustainability of water repellency is also a desirable characteristic thereof and various products have been developed from this standpoint (see, for example, Japanese Patent Kokai 59-30876). The improvement in the sustainability of water repellency in these products is obtained to some extent by utilizing a silicone resin to serve simultaneously as a water repellency-imparting ingredient and as a film forming agent but the improvement obtained thereby is still not satisfactory.

SUMMARY OF THE INVENTION

An object of the present invention accordingly is to provide a novel and improved film-forming agent capable of sustainedly exhibiting water repellency so that a single application thereof to human skin fully protects the skin from defatting even by repeated contacting with water.

Another object of the invention is to provide a film-forming agent capable of sustainedly exhibiting water repellency so as to be useful as an additive ingredient in a car-polishing wax and the like.

Thus, the film forming agent of the present invention is a blend which comprises: (a) 100 parts by weight of a silica organosol which is a dispersion of, in an organic solvent, from 1 to 50% by weight of spherical fine silica particles having an average particle diameter in the range from 1 to 100 nm and a specific surface area of at least 300 m$^2$/g and after a trimethylsilylating treatment of the surface to have a density of the trimethyl silyl groups in the range from 0.5 to 10 $\mu$ moles/m$^2$, density of the alkoxy groups in the range from 0.5 to 10 $\mu$ moles/m$^2$ and density of the silanol groups in the range from 0.5 to 5 $\mu$ moles/m$^2$; and (b) from 1 to 100 parts by weight of a diorganopolysiloxane having a viscosity in the range from 5 to 10,000 centistokes at 25° C. and terminated at each molecular chain end with a silanolic hydroxy group.

DETAILED DESCRIPTION OF THE PREFERRED EMBODIMENTS

As is described above, the essential ingredients in the inventive film-forming composition are (a) a silica organosol of which the silica particles have a trimethy)silylated surface and (b) a diorqanopolysiloxane terminated at each molecular chain end with a silanolic hydroxy group. By virtue of this unique formulation, the inventive film-forming agent sustainedly exhibits excellent water repellency so that it is useful in various applications where sustained water repellency is essential such as skin care preparations, medical treatment agents, polishing agents and the like.

The silica organosol, as an essential component in the inventive composition, can be prepared by the treatment of a silica sol obtained from an alkoxy silane as a starting material with, for example, trimethyl silanol. The silica organosol is a dispersion of spherical fine silica particles having an average particle diameter in the range from 1 to 100 nm and a specific surface area of at least 300 m$^2$/g in an organic solvent specified later. When the silica particles have an average particle diameter larger than 100 nm, the silica particles may eventually settle in the form of precipitates to decrease the stability of dispersion in the organic solvent so that a uniform film-forming composition can hardly be obtained. On the other hand, difficulties are encountered in the preparation of a silica organosol when the average particle diameter of the silica particles smaller than 1 nm is desired. The silica particles should preferably have an average particle diameter in the range from 5 to 50 nm. The silica particles also should have a specific surface area of at least 300 m$^2$/g because when the specific surface area is too small, the stability of silica particle dispersion in the organic solvent is decreased eventually to cause precipitation of the silica particles in the sol so that a uniform film-forming composition can hardly be obtained.

It is important that the spherical fine silica particles in the silica organosol have a controlled surface condition relative to the types of the surface groups and the densities thereof per unit surface area. For example, the density of silanolic surface groups is controlled by the partial alkoxylation of the inherent silanol groups on the surface of the silica particles so as to impart the silica particles with adequate compatibility with the hydroxy terminated diorqanopolysiloxane as the component (b) when the silica organosol and the diorganopolysiloxane are compounded together. Namely, the density of the silanol groups should be in the range from 0.5 to 5 $\mu$ moles/m$^2$. When the density of the silanol groups is too large, the silica particles, even after a trimethylsilylating treatment, may eventually cause agglomeration and precipitation in the composition as a consequence of recombination of the silanol groups on the silica surface. When the density of the silanol groups is too small, on the other hand, the composition cannot be imparted with sufficiently high film-formability.

In addition to the above mentioned limitation in the density of the silanol groups, the density of alkoxy groups also should be controlled in the range from 0.5 to 10 $\mu$ moles/m$^2$ by replacing the alkoxy groups with more bulky trimethyl silyl groups so that recombination of the silanol groups can be effectively prevented by the steric effect of the trimethyl silyl groups to increase the stability of the silica particle dispersion in the hydroxy-terminated diorganopolysiloxane and to impart the composition with good film-formability.

Trimethyl silyl groups on the surface of the silica particles increase the stability of silica particle dispersion in an organic solvent or, in particular, in a non alcoholic solvent along with an improving effect of the wettability of the silica surface with the hydroxy terminated diorganopolysiloxane contributing to the uniformity of the film obtained from the inventive film-forming composition after evaporation of the organic solvent. In this regard, the density of the trimethyl silyl groups should be in the range from 0.5 to 10 $\mu$ moles/m$^2$. When the density of the trimethyl silyl groups is too small, the silica particles would have poor compatibility with the organic solvent and the hydroxy terminated diorganopolysiloxane as a consequence of the decrease in the steric effect to be exhibited by the trimethyl silyl groups and the wettability of the silica surface with the hydroxy-terminated diorganopolysiloxane. Namely, the density of the trimethyl silyl groups should be at least 0.5 $\mu$ moles/m$^2$ from the standpoint of obtaining good stability of the silica sol and film-formability of the composition. On the other hand, the density of the trimethyl silyl groups can hardly exceed 10 $\mu$ moles/m$^2$ which is approximately the upper limit of the density by which trimethyl silyl groups can be introduced into the silica surface.

The organic solvent in the silica organosol as the component (a) is not particularly limitative provided that the surface treated spherical fine silica particles can be dispersed therein with good stability. Examples of suitable organic solvents include low molecular weight organopolysiloxanes, saturated aliphatic hydrocarbon solvents, aliphatic alcohols, aromatic hydrocarbon solvents and the like having a boiling point in the range from 70° C. to 300° C. under normal pressure. When the inventive composition is used in a preparation for skin care or for medical use, the solvent should have irritativeness against human skin as small as possible so that the organic solvent is selected preferably from low molecular-weight organopolysiloxanes and isoparaffins, i.e. saturated hydrocarbon solvents having a branched molecular structure. When the inventive composition is used as an additive of a polishing agent, for example, for car polishing, it is essential that the organic solvent contained in the composition has little adverse influences on the coating film of the car. In this regard, the organic solvent also should be selected preferably from low molecular weight organopolysiloxanes and saturated aliphatic hydrocarbon solvents.

Examples of the above mentioned low molecular weight organopolysiloxanes suitable as the organic solvent include oligomeric cyclic organopolysiloxanes such as hexamethyl cyclotrisiloxane, octamethyl cyclotetrasiloxane, decamethyl cyclopentasiloxane, dodecamethyl cyclohexasiloxane, trimethyl triethyl cyclotrisiloxane, hexaethyl cyclotrisiloxane, diethyl tetramethyl cyclotrisiloxane, dimethyl tetraethyl cyclotrisiloxane, diethyl hexamethyl cyclotetrasiloxane, tetraethyl tetramethyl cyclotetrasiloxane and the like, straightly linear organopolysiloxanes such as hexamethyl disiloxane, octamethyl trisiloxane, decamethyl tetrasiloxane, dodecamethyl pentasiloxane, tetradecamethyl hexasiloxane, hexaethyl disiloxane, octaethyl trisiloxane and the like and branched organopolysiloxanes such as methyl tris(trimethylsiloxy) silane, phenyl tris(trimethylsiloxy) silane and the like. These organopolysiloxanes can be used either singly or as a mixture of two kinds or more according to need. Among the above named ones, dimethyl polysiloxanes are particularly preferable.

Examples of the saturated aliphatic hydrocarbon solvents suitable as the organic solvent, on the other hand, include petroleum ether, ligroin, mineral spirit, kerosine, isoparaffins and the like. Although these saturated aliphatic hydrocarbon solvents can be used either singly or as a mixture of two kinds or more according to need, isoparaffins are particularly preferable among them because human skin is little irritated or the paint-coated surface of automobiles is little attacked thereby. Various isoparaffin solvents are available as a commercial product sold under the trade names of, for example, Isopars C. E. G. H. L and M supplied by Exxon Chemical Co., IP Solvents 1016, 1620 and 2028 supplied by Idemitsu Petrochemical Co., Markasol R supplied by Maruzen Petrochemical Co., Nisseki Isosols 300 and 400 supplied by Nippon Petrochemical Co. and Shellsol 71 supplied by Shell Chemical Co.

The silica organosol contains the spherical fine silica particles in an amount in the range, preferably, from 1 to 50% by weight or, more preferably, from 10 to 30% by weight. When the content of silica particles is too small in the silica sol, the film formed from the film-forming composition is sometimes uneven or irregular not to be imparted with full water repellency. When the content of silica particles is too large in the silica sol, on the other hand, condensation reaction of the silanol groups on the surface of the silica particles may take place between silica particles resulting in agglomeration of the silica particles not to give a uniform film when the film-forming composition is used.

The diorganopolysiloxane used as the component (b) in the inventive film forming agent has a viscosity in the range from 5 to 10,000 centistokes at 25° C. and is terminated at each molecular chain end with a hydroxy group. The diorganopolysiloxane is selected preferably from dimethyl polysiloxanes, diethyl polysiloxanes, ethyl methyl polysiloxanes, copolymers of diethyl siloxane units and dimethyl siloxane units and the like, of which hydroxy-terminated dimethyl polysiloxanes are preferable. When the viscosity thereof is too low, the composition prepared by using the same cannot be imparted with good film-formability. When the viscosity is too high, on the other hand, a disadvantage is caused that the film formed from the composition cannot be completely free from tackiness. The diorganopolysiloxane preferably has a viscosity in the range from 10 to 1000 centistokes at 25° C.

The amount of the hydroxy-terminated diorganopolysiloxane in the inventive film-forming agent is in the range from 1 to 100 parts by weight or, preferably, from 5 to 50 parts by weight per 100 parts by weight of the silica organosol as the component (a). When the amount of the hydroxy-terminated diorganopolysiloxane is too small, no uniformity can be obtained in the film formed from the composition. When the amount thereof is too large, on the other hand, the film formed from the composition has tackiness more or less.

The inventive film-forming agent can be prepared by uniformly blending the silica organosol as the component (a) and the hydroxy terminated diorganopolysiloxane as the component (b) at room temperature or, if necessary, under heating. These two components have good compatibility with each other so that the blending of them can be performed by using any conventional liquid blending machines and no special blending machine need be used.

The inventive film forming agent can optionally be admixed with various kinds of known additives each in a limited amount. Examples of such optional additives include silicone fluids to improve the surface luster of the film formed from the inventive film-forming composition, waxes such as carnauba wax, montan wax and the like, pigments, dyes, perfumes, medicinal ingredients, volatilizable materials and so on.

The film forming agent of the present invention forms, after evaporation of the organic solvent, a uniform film having good water repellency with sustainability as composed of a diorganopolysiloxane and spherical fine silica particles having a specific average particle diameter and silanol groups on the surface in a specific density so that it is useful in the applications to cosmetic and skin-care preparations, medical uses, polishing agents and the like.

The following examples are given to illustrate the inventive film forming agent in more detail, but not to limit the scope of the invention in any way. The values of viscosity appearing in the following description are all those obtained by the measurement at 25° C.

EXAMPLE 1

Into a glass-made flask of 10 liter capacity equipped with a stirrer, dropping funnel and thermometer were introduced 84 g of 29% ammonia water, 200 g of deionized water and 4500 g of ethyl alcohol. The mixture in the flask was kept at 35° C. and a mixture of 560 g of tetramethoxy silane and 510 g of ethyl alcohol was added dropwise into the mixture under vigorous agitation over a period of about 1 hour followed by further continued agitation for an additional 30 minutes to give a silica sol in ethyl alcohol. Thereafter, 132 g of trimethyl silanol were gradually added to the silica sol which was then agitated for 5 hours at room temperature. After the end of this period for agitation, the silica sol was concentrated on a rotary evaporator to give a concentrated silica sol in ethyl alcohol containing 27% by weight of silica, which is referred to as the ethanol sol I hereinbelow.

A 300 g portion of this ethanol sol 1 was admixed with 270 g of octamethyl cyclotetrasiloxane and the mixture was subjected to distillation under reduced pressure in a stainless steel-made packed column having an inner diameter of 28 mm and a height of 750 mm so as to replace the ethyl alcohol in the ethanol sol I with the octamethyl cyclotetrasiloxane. The thus obtained silica sol, which is referred to as the silica organosol I hereinbelow, contained 25% by weight of silica. The silica organosol I was a colorless clear liquid having a viscosity of 10 centistokes. With an object to determine the specific surface area and the densities of the substituent groups on the silica particles, the solvent in the silica organosol I was evaporated to dryness by heating at 150° C. under a reduced pressure of 5 mmHg. The thus obtained silica particles, of which the average particle diameter was 9.5 nm as determined by the electron microscopic examination, had a specific surface area of 420 m$^2$/g according to the result of the measurement by the BET method by nitrogen absorption. Densities of the silanol groups, ethoxy groups and trimethyl silyl groups on the surface of the silica particles were 2.4 $\mu$ moles/m$^2$, 5.7 $\mu$ moles/m and 2.4 $\mu$ moles/m$^2$, respectively. The method for the determination was as follows. Firstly, the silica particles were heated suspended in methyl alcohol and the suspension was heated in an autoclave at 150° C. for 8 hours and the the content of the hydroxy groups was calculated from the increase in the content of carbon by this methyl alcohol treatment. Further, the dried silica particles were dissolved in a 10% by weight aqueous solution of sodium hydroxide at room temperature and the isolated ethyl alcohol, methylsilane compounds and methylsiloxane compounds in the alkali solution were extracted and gas-chromatographically analyzed to determine the contents of the ethoxy groups and trimethyl silyl groups.

A 100 g portion of the silica organosol 1 was admixed with 18 g of a first hydroxy-terminated dimethylpolysiloxane having a viscosity of 45 centistokes, referred to as the siloxane A hereinbelow, and 6 g of a second hydroxy terminated dimethylpolysiloxane having a viscosity of 680 centistokes. referred to as the siloxane B hereinbelow, to give a uniform mixture. A 1 g portion of this mixture was taken in an aluminum-made dish having a diameter of 60 mm and a depth of 10 mm and kept for 3 hours in a hot-air circulation oven controlled at 105° C. to give a uniform, colorless and transparent film which had no cracks and was free from tackiness on the surface.

The same mixture as above was thinly spread over the skin of a human hand with a finger tip and the coated hand was repeatedly washed with warm water at about 35° C. by using toilet soap to find that the hand skin was fully water repellent even after 10 times of repeated washing. This result supported the conclusion that the film-forming agent could exhibit water repellency with good sustainability. Such sustained water repellency could not be obtained with any commerically available skin care preparations.

EXAMPLE 2

Another film-forming composition was prepared in the same formulation as in Example 1 except that the siloxane B was omitted and the amount of the siloxane A was increased to 30 g instead. The result of the film-forming test therewith on an aluminum made dish was as good as in Example 1.

EXAMPLE 3

A further film-forming composition was prepared in the same formulation as in Example 1 except that the amount of the siloxane B was decreased to 4 g and, instead, 4 g of a trimethylsilyl terminated dimethylpolysiloxane having a viscosity of 500 centistokes were added. The result of the film-forming test therewith on an aluminum-made dish was as good as in Example 1.

EXAMPLE 4

A 300 g portion of the ethanol sol 1 obtained in Example 1 was admixed with 710 g of IP Solvent 2028 (a product by Idemitsu Petrochemical Co.) and the mixture was subjected to distillation under reduced pressure to replace the ethyl alcohol with the IP Solvent 2028. The thus obtained silica sol, which is referred to as the silica organosol II hereinbelow, contained 11% by weight of silica. This silica organosol II was a translucent liquid having a viscosity of 52 centistokes. The silica particles contained in the sol were spherical particles having an average particle diameter of 10.5 nm as examined with an electron microscope and had a specific surface area of 430 m /g as determined in the same manner as in Example 1. The densities of silanol groups, ethoxy groups and trimethyl silyl groups on the surface of the silica particles were 1.8 $\mu$ moles/m$^2$, 5.4 $\mu$ moles/m$^2$ and 2.4 $\mu$ moles/m$^2$, respectively.

A film-forming composition was prepared by uniformly blending 100 g of the silica organosol II, 10 g of the hydroxy-terminated siloxane A used in Example 1 and 4 g of the hydroxy-terminated siloxane B used in Example 1 and a film was formed therefrom on an aluminum-made dish in the same manner as in Example 1. The properties of this film were as satisfactory as in Example 1.

EXAMPLE 5

A film forming composition was prepared and a film was formed therefrom in the same manner as in Example 4 described above except that the amount of the siloxane A was increased to 12 g with omission of the siloxane B and 3 g of a trimethyl silyl-terminated dimethyl polysiloxane having a viscosity of 350 centistokes were additionally added. The properties of the thus formed film were as satisfactory as in Example 4.

EXAMPLE 6

A film forming composition was prepared and a film was formed therefrom in the same manner as in Example 4 except that the amount of each of the siloxanes A and B was increased to 5 g and 8 g, respectively. The properties of the thus formed film were as satisfactory as in Example 4.

COMPARATIVE EXAMPLE 1

The experimental procedure was just the same as in Example 2 except that the amount of the siloxane A was decreased to 0.8 g. The film formed from the film-forming composition on an aluminum-made dish had a large number of cracks and could readily be peeled off from the aluminum dish.

COMPARATIVE EXAMPLE 2

The experimental procedure was just the same as in Example 2 except that the amount of the siloxane A was increased to 105 g. An attempt to form a film from the composition on an aluminum-made dish failed to give a film due to the extreme stickiness of the composition after evaporation of the solvent.

COMPARATIVE EXAMPLE 3

A silica sol in ethyl alcohol containing 20% by weight of silica, which is referred to as the ethanol sol II here inbelow, was prepared in the same manner as in the preparation of the ethanol sol I in Example 1 except that the amount of 29% ammonia water was increased to 330 g with omission of the deionized water, the amount of the ethyl alcohol was decreased to 4300 g and the reaction temperature was 20° C. instead of 35° C.

A silica organosol containing 25% by weight of silica, which is referred to as the silica organosol III hereinbelow, was prepared in the same manner as in the preparation of the silica organosol I in Example 1 from 300 g of the ethanol sol II and 220 g of octamethyl cyclotetrasiloxane by distillation under reduced pressure to replace the ethyl alcohol with octamethyl cyclotetrasiloxane. The thus obtained silica organosol III was a milky white liquid having a viscosity of 4 centistokes and the silica particles dispersed therein had an average particle diameter of 180 nm and a specific surface area of 325 m /g. The densities of the silanol groups, ethoxy groups and trimethyl silyl groups on the surface of the silica particles were 0.6 $\mu$ mole/m$^2$, 5.0 $\mu$ moles/m$^2$ and 4.2 $\mu$ moles/m$^2$, respectively.

A film-forming composition was prepared in the same formulation as in Example 1 excepting replacement of the silica organosol I with the same amount of the silica organosol III prepared above in combination with the siloxanes A and B. The composition was spread over an aluminum-made dish and converted into a film in the same manner as in Example 1 to find that the film was opaque and non-uniform with a lumpy appearance and stickiness on the surface to be inferior in quality as compared with the film obtained in Example 1.

What is claimed is:

1. A film-forming agent which comprises:
   (a) 100 parts by weight of a silica organosol which is a dispersion of, in an organic solvent, from 1 to 50% by weight of spherical fine silica particles having an average particle diameter in the range from 1 to 100 nm and a specific surface area of at least 300 m$^2$/g and wherein after a trimethylsilylating treatment of the surface of said silica organosol said treated surface will have a density of the trimethyl silyl groups in the range from 0.5 to 10 $\mu$ moles/m$^2$, density of the alkoxy groups in the range from 0.5 to 10 $\mu$ moles/m$^2$ and density of the silanol groups in the range from 0.5 to 5 $\mu$ moles/m$^2$; and
   (b) from 1 to 100 parts by weight of a diorganopolysiloxane having a viscosity in the range from 5 to 10,000 centistokes at 25° C. and terminated at each molecular chain end with a silanolic hydroxy group.

2. The film-forming agent as claimed in claim 1 wherein the organic solvent has a boiling point in range from 70° to 300° C. and is selected from the group consisting of organopolysiloxanes, saturated aliphatic hydrocarbon solvents, aliphatic alcohols and aromatic hydrocarbon solvents.

3. The film-forming agent as claimed in claim 2 wherein the organopolysiloxanes having a boiling point in the range from 70° to 300° C. is octamethyl cyclotetrasiloxane.

4. The film-forming agent as claimed in claim 1 wherein the silica organosol contains from 10 to 30% by weight of the silica particles.

5. The film-forming agent as claimed in claim 1 wherein the diorganopolysiloxane as the component (b) has a viscosity in the range from 10 to 1000 centistokes at 25° C.

6. The film-forming agent as claimed in claim 1 wherein the amount of the diorqanopolysiloxane as the component (h) is in the range from 5 to 50 parts by weight per 100 parts by weight of the silica organosol as the component (a).

* * * * *